United States Patent
Al Sabti

(10) Patent No.: US 10,624,783 B2
(45) Date of Patent: Apr. 21, 2020

(54) MULTIPORT VITRECTOMY CUTTER

(71) Applicant: Khalid Al Sabti, Mubarak Al Abdulla (KW)

(72) Inventor: Khalid Al Sabti, Mubarak Al Abdulla (KW)

( * ) Notice: Subject to any disclaimer, the term of this patent is extended or adjusted under 35 U.S.C. 154(b) by 0 days.

(21) Appl. No.: 16/568,190

(22) Filed: Sep. 11, 2019

(65) Prior Publication Data

US 2020/0000636 A1 Jan. 2, 2020

Related U.S. Application Data

(63) Continuation of application No. PCT/US2018/021181, filed on Mar. 6, 2018.

(51) Int. Cl.
*A61F 9/007* (2006.01)

(52) U.S. Cl.
CPC .................. *A61F 9/00736* (2013.01)

(58) Field of Classification Search
CPC .............. A61F 9/00736; A61F 9/00745; A61F 9/00754; A61F 9/00763; A61F 9/008; A61B 17/3207
See application file for complete search history.

(56) References Cited

U.S. PATENT DOCUMENTS

| | | | | |
|---|---|---|---|---|
| 5,106,364 A | * | 4/1992 | Hayafuji | A61B 17/32002 30/208 |
| 5,458,112 A | * | 10/1995 | Weaver | A61B 10/0275 600/566 |
| 5,843,111 A | | 12/1998 | Vijvinkel | |
| 8,888,802 B2 | | 11/2014 | Underwood et al. | |
| 9,668,918 B2 | | 6/2017 | Geuder | |
| 2007/0185514 A1 | | 8/2007 | Kirchhevel | |
| 2014/0171997 A1 | * | 6/2014 | Nissan | A61F 9/00763 606/171 |
| 2014/0364885 A1 | * | 12/2014 | Wells | A61F 9/00754 606/170 |
| 2015/0182379 A1 | | 7/2015 | Fantoni et al. | |
| 2015/0335485 A1 | | 11/2015 | Rieger et al. | |
| 2016/0022489 A1 | | 1/2016 | Hartstra | |
| 2016/0135991 A1 | | 5/2016 | Farley et al. | |
| 2017/0172796 A1 | | 6/2017 | Biancalana et al. | |
| 2017/0312131 A1 | | 11/2017 | Maholtra | |

FOREIGN PATENT DOCUMENTS

KR 102014002707 A 1/2014

* cited by examiner

*Primary Examiner* — Katrina M Stransky
(74) *Attorney, Agent, or Firm* — Richard C. Litman; Nath, Goldberg & Meyer

(57) ABSTRACT

The multiport vitrectomy cutter (10) is an ocular surgical tool allowing a surgeon to select between a single cutting port configuration and a multiple cutting port configuration. The multiport vitrectomy cutter includes an internal tube (36) and a rotating external tube (22). The external tube has a plurality of external ports (28, 30, 32) for receiving vitreous of the eye. The internal tube (36) has a closed distal end (38), defining a cutting blade, and is slidably disposed within the external tube (22) so that the cutting blade oscillates across a first one of the external ports (28) to cut tissue. The internal tube (36) has at least one internal port (40, 42), such that selective rotation of the external tube (22) with respect to the internal tube (36) selectively aligns the at least one internal port (40, 42) with a remainder of the external ports (30, 32).

3 Claims, 9 Drawing Sheets

MULTIPORT VITRECTOMY CUTTER

CROSS REFERENCE TO RELATED APPLICATION

This application is a continuation of International patent application serial no. PCT/US2018/021181, filed Mar. 6, 2018.

TECHNICAL FIELD

The disclosure of the present patent application relates to surgical tools, and particularly to a vitrectomy cutter having a user selectable number of cutting ports.

BACKGROUND ART

A vitrectomy is a surgical procedure to remove some or all of the vitreous humor from the eye. FIG. 2 illustrates a conventional vitrectomy surgical system 100, which includes a base housing 102 and an associated display screen 104, typically used to show data relating to system operation and performance during a vitrectomy surgical procedure. The surgical system 100 further includes a vitrectomy cutter system 110 that includes a vitrectomy cutter 112. As illustrated in FIG. 3, the vitrectomy cutter system 110 includes the vitrectomy cutter 112, a pneumatic pressure source 120, a cutter driver (shown as an adjustable directional on-off pneumatic driver 122), a muffler 124 and a controller 126. The source 120, driver 122, muffler 124, and the cutter 112 are in fluid communication with each other (shown along lines representing flow paths or flow lines). The controller 126 is in electrical communication with the driver 122.

As shown in FIG. 4, the conventional prior art vitrectomy cutter 112 is a pneumatically driven cutter that operates by receiving pneumatic pressure alternating through first and second ports 140 and 142. The cutter 112 has a cutting portion 150, which includes an outer cutting tube 152, an inner cutting tube 154, and a reciprocating air-driven diaphragm 156, all partially encased by a housing 158. The housing 158 includes an end piece 160 at the cutter's proximal end with the first and second air supply ports 140, 142 and one suction port 162.

The cutting portion 150 extends from the housing 158 and includes a distal end 166. FIG. 5 shows the distal end 166 of the cutting portion 150 in greater detail. As shown, the inner cutting tube 154 fits within the outer cutting tube 152 in a coaxial manner, and the inner cutting tube 154 is axially moveable relative to the outer cutting tube 152. As shown in FIGS. 5 and 6, the outer cutting tube 152 has a closed end 164 and an outer port 168 that receives tissue, such as ophthalmic tissue. The outer port 168 is in fluid communication with an inner channel 170 of the outer cutting tube 152. As shown, port 168 is typically oval shaped and is configured to cooperate with the inner cutting tube 154 to cut tissue during an ophthalmic surgery. The distal and proximal edges of port 168 may be sharpened to aid in the cutting of the vitreous. As shown, extending from inner cutting tube 154, is a connector 194 which is tipped with a cutting blade 208 having respective distal and proximal cutting edges 216, 218.

Conventional vitrectomy cutters, such as vitrectomy cutter 112, employ a single port, such as port 168, on a single side of the outer cutting tube. However, in some procedures, the surgeon may be assisted by having access to multiple ports, which would remove the necessity of the surgeon rotating the vitrectomy device to align the port in a desired radial direction, as may be necessary. Rather than providing the surgeon with separate vitrectomy cutters, one with only a single port and one with multiple ports, dependent upon the particular surgical procedure, it would obviously be desirable to have a single device which may be used in either a single port mode or a multiple port mode. Thus, a multiport vitrectomy cutter solving the aforementioned problems is desired.

DISCLOSURE

The multiport vitrectomy cutter is an ocular surgical tool allowing a surgeon to select between a single cutting port configuration and a multiple cutting port configuration. The multiport vitrectomy cutter includes a main body having a proximal portion and a distal portion. The proximal portion is adapted for gripping by the surgeon's hand and the distal portion is divided into a fixed portion, which is fixed with respect to the proximal portion, and a rotating portion which selectively rotates with respect to the fixed portion (and the proximal portion of the main body).

An external tube extends from the rotating portion of the distal portion of the main body for penetrating an eye of a patient during an ocular surgical procedure. The external tube has a closed distal end and an open proximal end. The external tube further has a plurality of external ports for receiving vitreous of the eye during the ocular surgical procedure. Each of the external ports is located a unique axial distance from the closed distal end, and each of the external ports is also angularly misaligned about a central axis of the external tube with respect to one another.

An internal tube, having a closed distal end defining a cutting blade, is slidably disposed within the external tube so that the cutting blade oscillates across a first one of the external ports of the external tube to cut tissue. The first one of the external ports is the port having the least axial distance from the closed distal end of the external tube. The internal tube has at least one internal port, such that selective rotation of the external tube with respect to the internal tube selectively aligns the at least one internal port with a remainder of the external ports. The at least one internal port is defined by a cutting edge adapted to cut tissue. A pneumatically-driven diaphragm is secured to a proximal end of the internal tube for driving the internal tube in a reciprocating motion relative to the external tube.

These and other features of the present disclosure will become readily apparent upon further review of the following specification and drawings.

BRIEF DESCRIPTION OF THE DRAWINGS

Similar reference characters denote corresponding features consistently throughout the attached drawings.

BEST MODES

Figure 1:
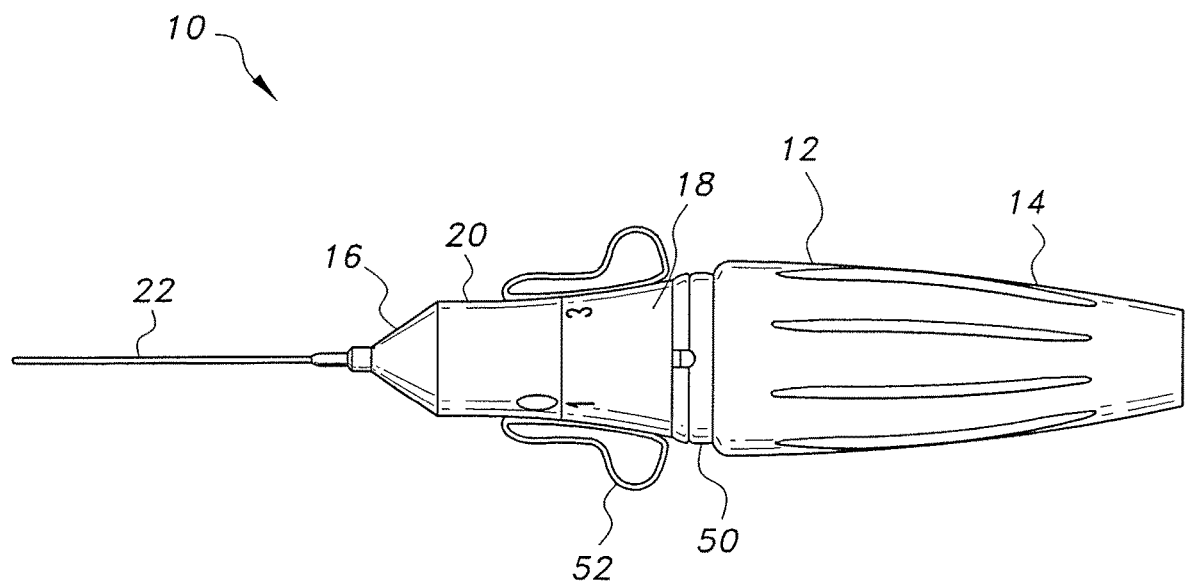
FIG. 1 is a side view of a multiport vitrectomy cutter.
Figure 2:
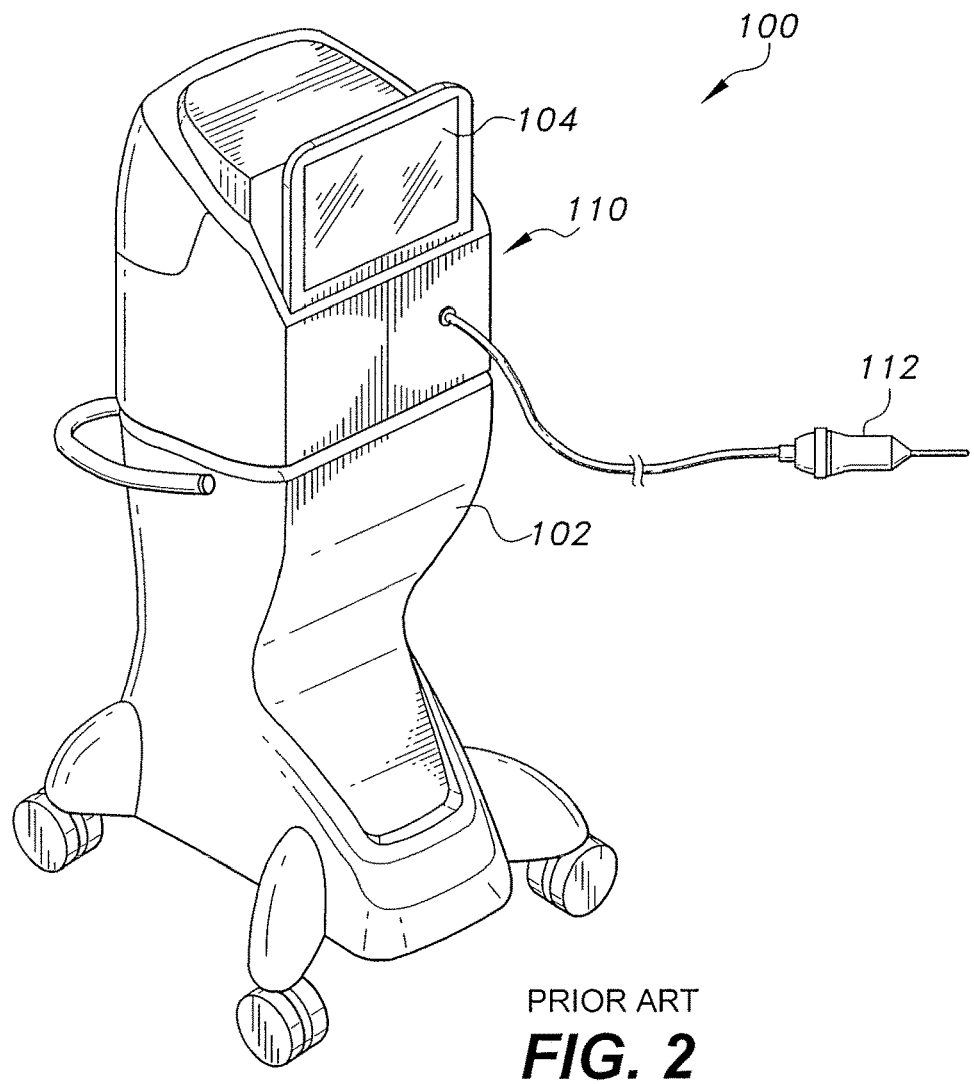
FIG. 2 is a perspective view of a prior art vitrectomy surgical system.
Figure 3:
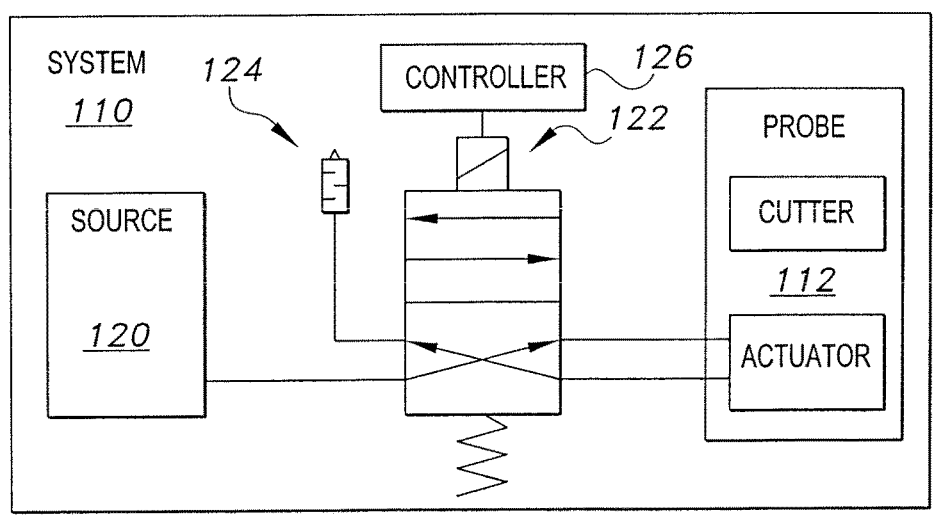
FIG. 3 schematically illustrates the prior art vitrectomy surgical system of FIG. 2.
Figure 7:
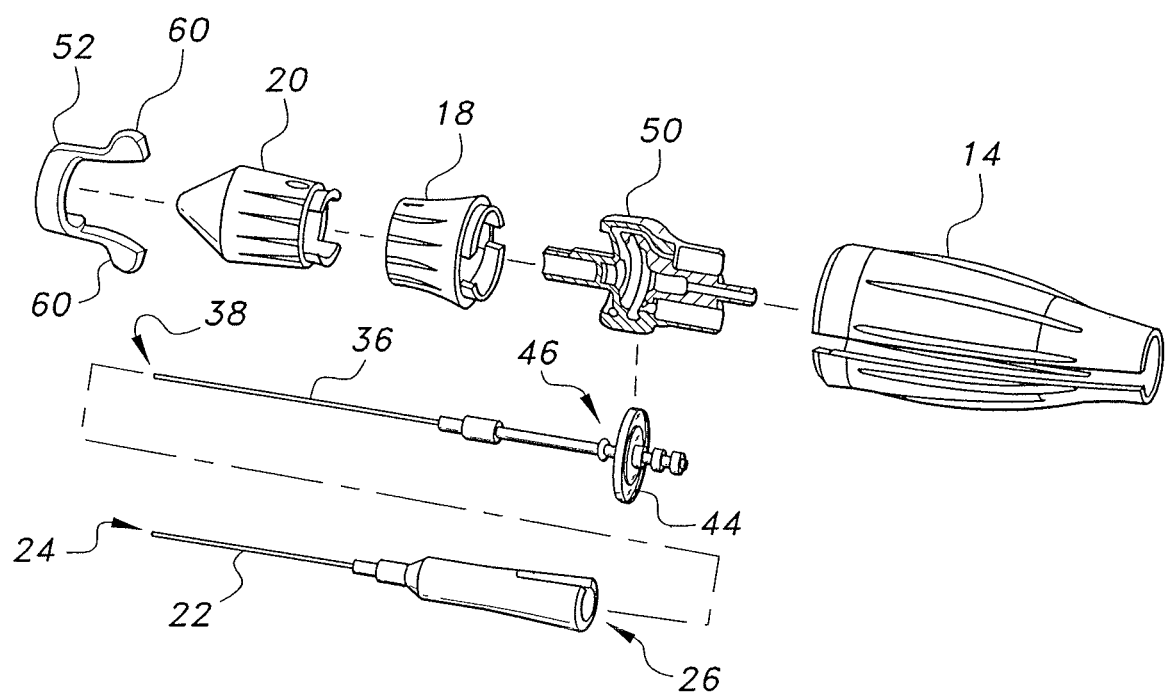
FIG. 7 is an exploded perspective view of the multiport vitrectomy cutter.

As best shown in FIGS. 1 and 7, the multiport vitrectomy cutter 10 is an ocular surgical tool allowing a surgeon to select between a single cutting port configuration and a multiple cutting port configuration. The multiport vitrectomy cutter 10 includes a main body 12 having a proximal portion 14 and a distal portion 16. The proximal portion 14 is adapted for gripping by the surgeon's hand and the distal portion 16 is divided into a fixed portion 18, which is fixed with respect to the proximal portion 14, and a rotating portion 20 which selectively rotates with respect to the fixed portion 18 (and the proximal portion 14 of the main body 12). It should be understood that the overall contouring and relative dimensions of the main body 12 are shown for exemplary purposes only.

Figure 8:
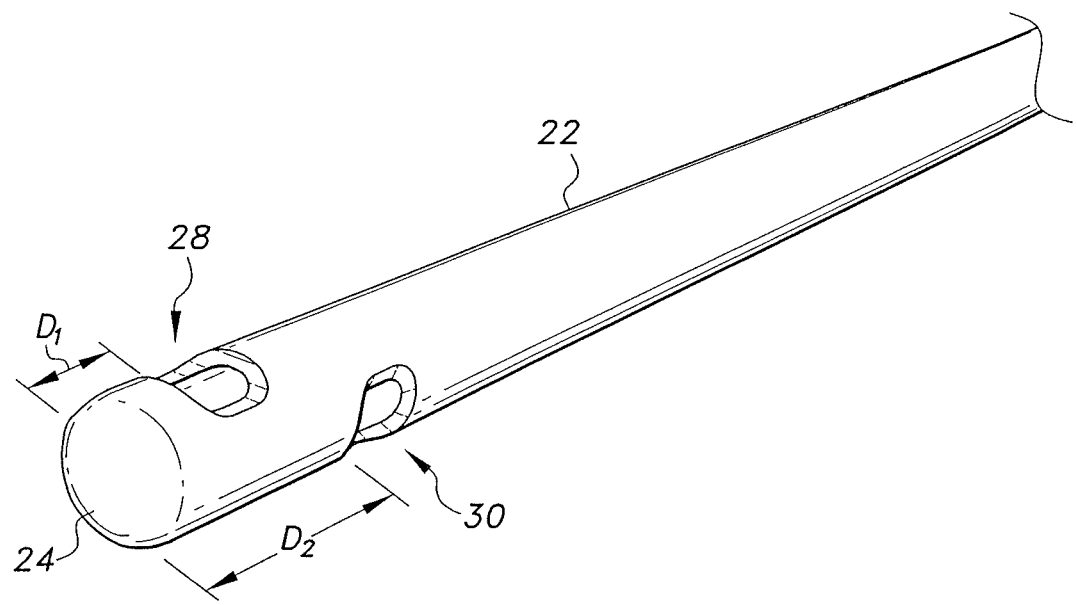
FIG. 8 is a perspective view of an external tube of the multiport vitrectomy cutter.
Figure 9:
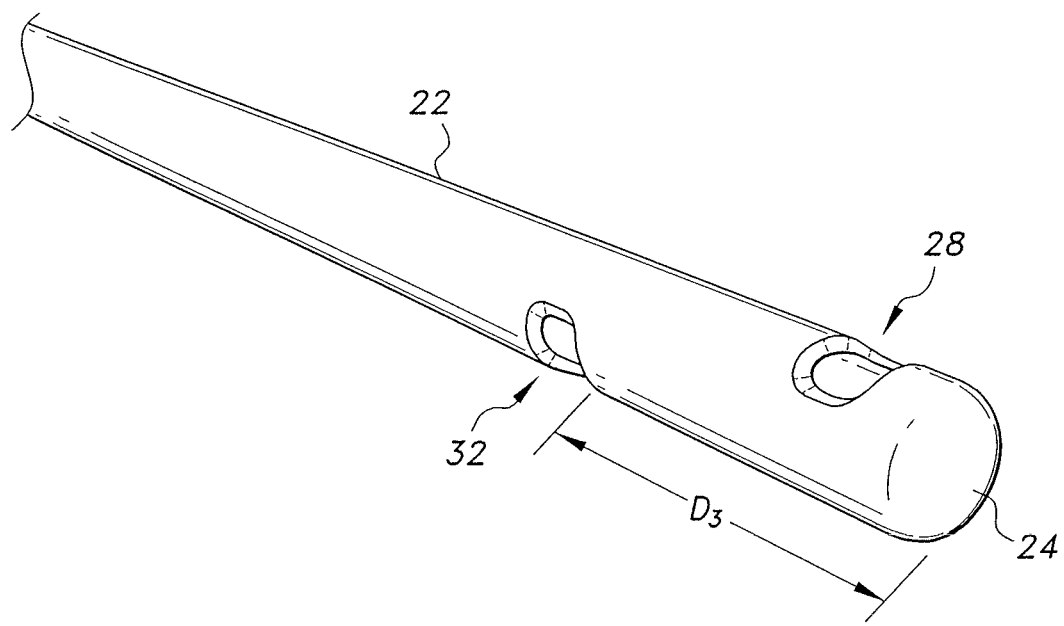
FIG. 9 is a perspective view of an external tube of the multiport vitrectomy cutter.
Figure 10:
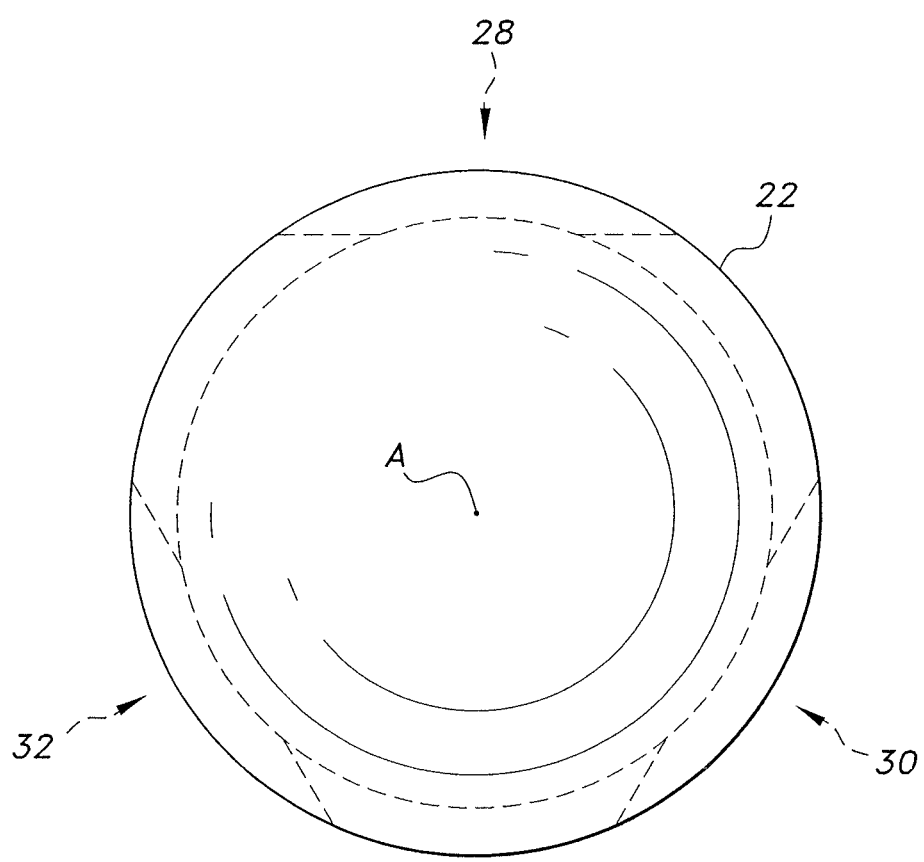
FIG. 10 diagrammatically illustrates positioning of external ports formed through the external tube of FIGS. 8 and 9.

An external tube 22 extends from the rotating portion 20 of the distal portion 16 of the main body 12 for penetrating an eye of a patient during an ocular surgical procedure. As best shown in FIGS. 8 and 9, the external tube 22 has a closed distal end 24 and an open proximal end 26 (seen in FIG. 7). The external tube 22 further has a plurality of external ports for receiving vitreous of the eye during the ocular surgical procedure. In the non-limiting example shown in FIGS. 8, 9, 11 and 12, three external ports 28, 30, 32 are shown. It should be understood that any desired number of external ports greater than one may be formed through external tube 22. Further, it should be understood that the contouring and relative dimensions of each port 28, 30, 32 are shown for exemplary purposes only. As seen in FIGS. 8 and 9, each of the external ports is located a unique axial distance from the closed distal end 24. In the non-limiting example of FIGS. 8 and 9, in which three external ports are formed through external tube 22, port 28 is positioned an axial distance $D_1$ from closed distal end 24, port 30 is positioned an axial distance $D_2$ from closed distal end 24, and port 32 is positioned an axial distance $D_3$ from closed distal end 24. Additionally, as best illustrated in FIG. 10, each of the external ports 28, 30, 32 is also angularly misaligned about a central axis A of the external tube 22 with respect to one another. In the non-limiting example of FIG. 10, external ports 28, 30, 32 are separated from adjacent ones of one another, about central axis A, by an angle of 120°, however it should be understood that this angular arrangement is shown for exemplary purposes only. As will be described in greater detail below, the angular misalignment of external ports 28, 30, 32 and their differing axial positions allows an internal tube 36, with its own internal ports 40, 42, to rotate with respect to external tube 22 for selective alignment or misalignment between the external ports and the internal ports.

Figure 11:
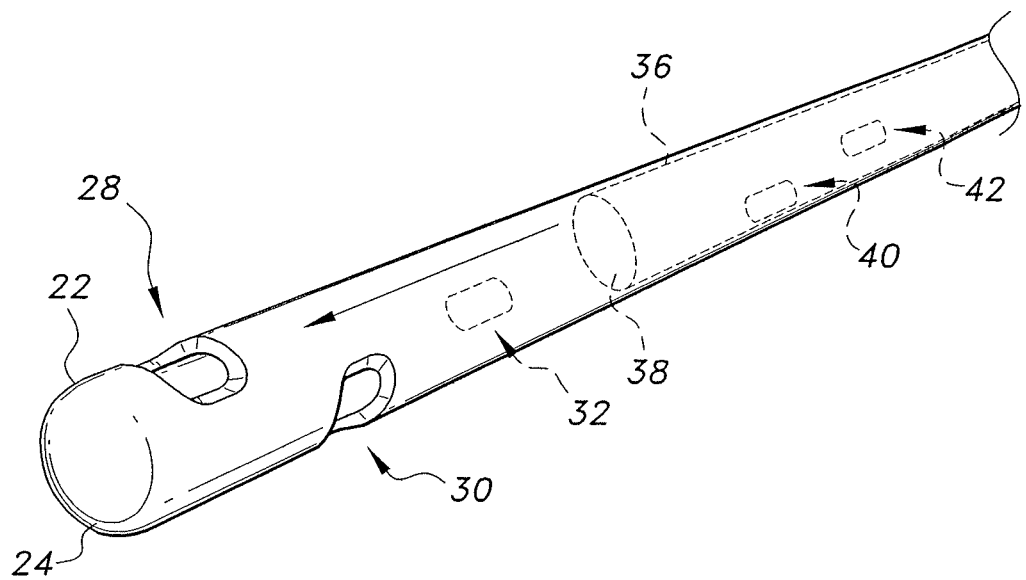
FIG. 11 is a partial perspective view of the multiport vitrectomy cutter, shown operating in a multiple cutting port configuration.
Figure 12:
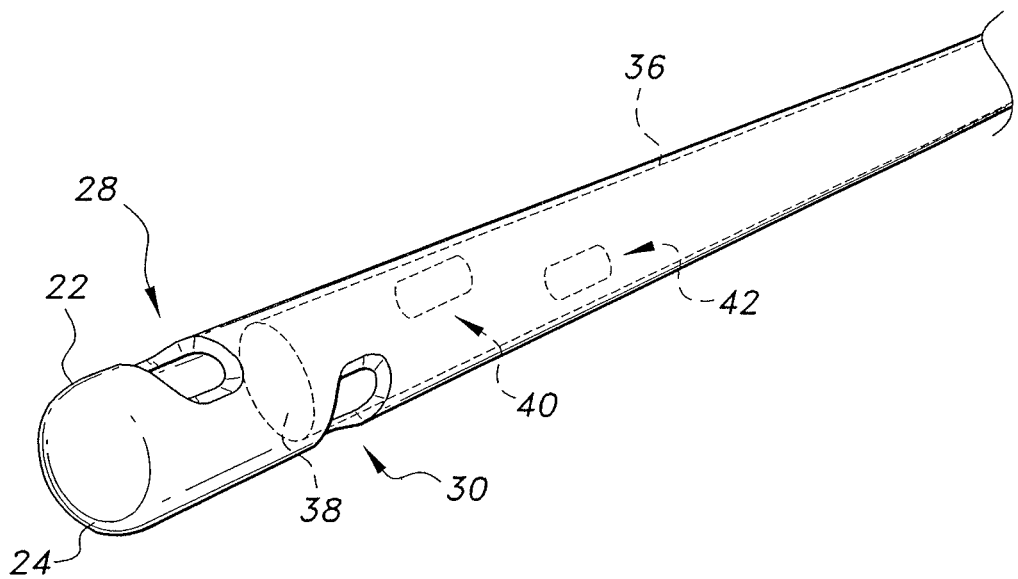
FIG. 12 is a partial perspective view of the multiport vitrectomy cutter, shown operating in a single cutting port configuration.

As best shown in FIGS. 11 and 12, internal tube 36 has a closed distal end 38, defining a cutting blade, and is slidably disposed within the external tube 22 so that the cutting blade oscillates across a first one of the external ports of the external tube 22 to cut tissue. The first one of the external ports is the port having the least axial distance from the closed distal end 24 of the external tube 22; i.e., external port 28, which is positioned distance $D_1$ from closed distal end 24 in the three port example shown in the Figures. The internal tube 36 has at least one internal port, such that selective rotation of the external tube 22 with respect to the internal tube 36 selectively aligns the at least one internal port with a remainder of the external ports. In the three external port example of FIGS. 11 and 12, FIG. 11 shows a multiport configuration in which internal ports 40, 42 are aligned with external ports 30, 32. Each of the internal ports is defined by a cutting edge adapted to cut tissue. Thus, in this configuration, as the internal tube 36 oscillates axially within the external tube 22, the cutting blade 38 passes back and forth beneath first external port 28, allowing tissue to enter first external port 28 and be cut by cutting blade 38. Additionally, with internal ports 40, 42 aligned with external ports 30, 32, tissue may also enter external ports 30, 32 and be cut by the cutting edges defining internal ports 40, 42.

When the surgeon wishes to switch to a single cutting port configuration, the surgeon rotates rotating portion 20 with respect to fixed portion 18, thus misaligning internal ports 40, 42 with respect to external ports 30, 32 (as shown in FIG. 12). In this configuration, as internal tube 36 reciprocates within external tube 22, the cutting edges defining internal ports 40, 42 are now each covered by the tubular body of external tube 22, leaving only external port 28 available for cutting. As in the multiport configuration, the cutting blade 38 oscillates across first external port 28 of the external tube 22 to cut tissue. Corresponding to the three external port example, and the exemplary 120° angular spread shown in FIG. 10, external tube 22 may rotate over a range of about 100° with respect to internal tube 36.

Figure 13:
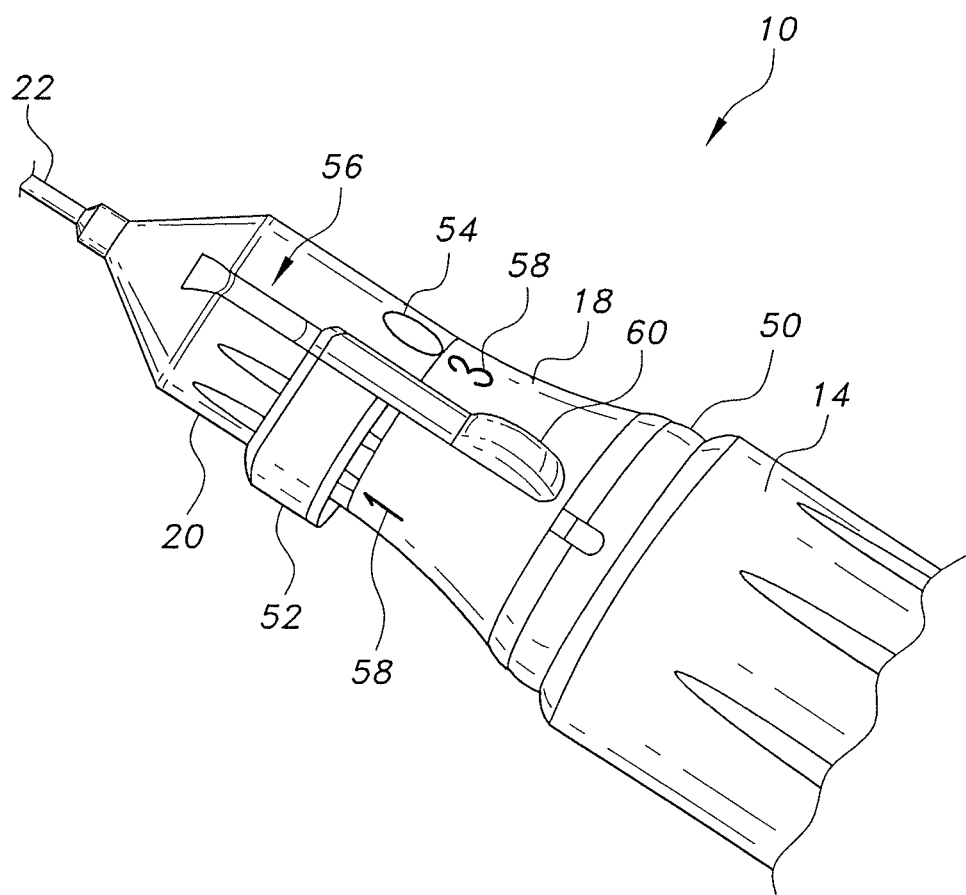
FIG. 13 is a partial perspective view of the multiport vitrectomy cutter.

As shown in FIGS. 1, 7 and 13, a gripping handle 52 may be secured to rotating portion 20, providing the surgeon with a gripping surface for easily rotating the rotating portion 20 with respect to fixed portion 18. In FIG. 13, one or more grooves 56 are shown formed in distal portion 16 of main body 12, allowing gripping handle 52 to be clipped on, and securely held by, distal portion 16, although it should be understood that gripping handle 52 may be secured to rotating portion 20 by any suitable method. In this example, gripping handle 52 is provided with arms 60 which may be releasably locked within a corresponding pair of grooves 56, allowing the surgeon to releasably lock rotating portion 20 with respect to fixed portion 18. Additionally, as shown in FIG. 13, the particular configuration of multiport vitrectomy cutter 10 may be indicated by a visual indicator, such as window 54, by indicia 58, or the like.

Figure 4:
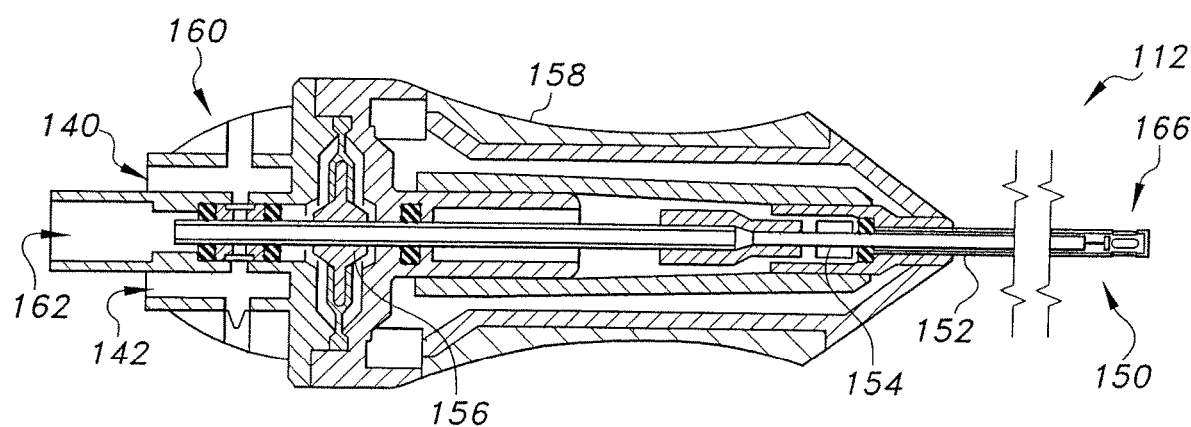
FIG. 4 is a side view in section of a prior art vitrectomy cutter of the prior art vitrectomy surgical system of FIG. 2.
Figure 5:
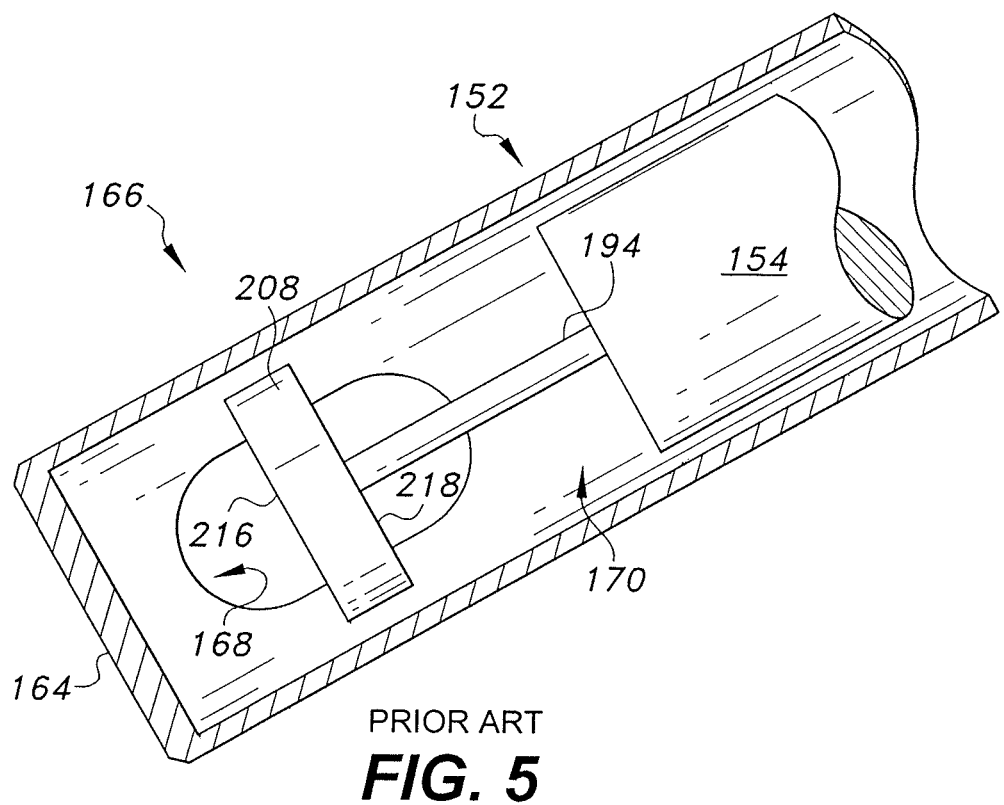
FIG. 5 is a partial sectional view of the prior art vitrectomy cutter of FIG. 4.
Figure 6:
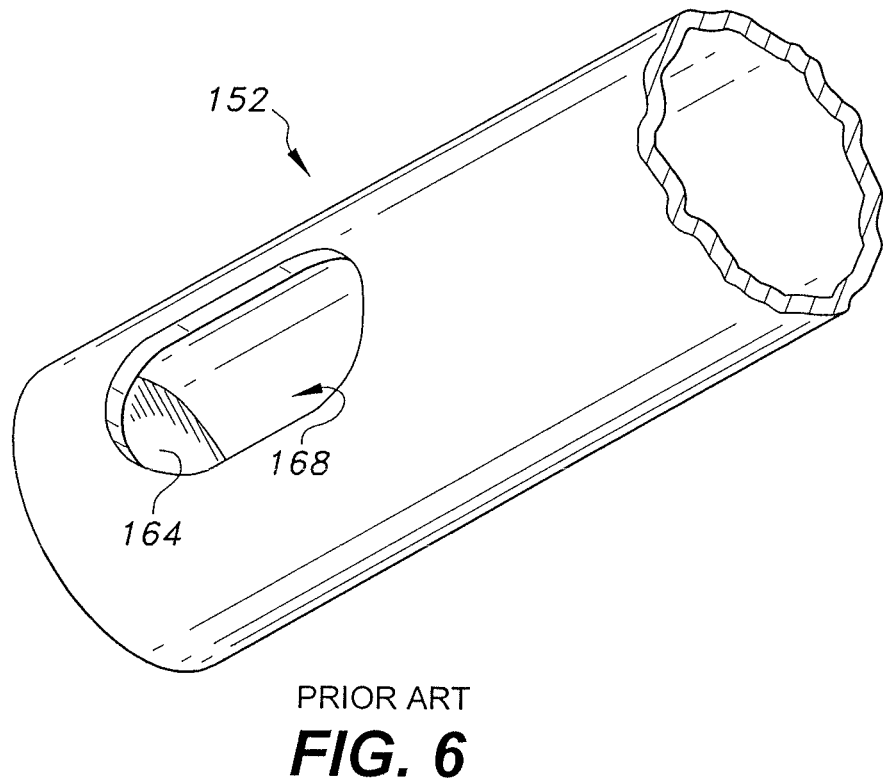
FIG. 6 is a partial perspective view of an external tube of the prior art vitrectomy cutter of FIG. 4.

Similar to vitrectomy cutter 112 of FIG. 4, multiport vitrectomy cutter 10 includes a pneumatically-driven diaphragm 44 secured to a proximal end 46 of the internal tube 36 for driving the internal tube 36 in a reciprocating motion relative to the external tube 22. It should be understood that any suitable type of pneumatic drive system may be used, such as that described above with regard to prior art vitrectomy cutter 112. As best seen in FIG. 7, a diaphragm housing 50 is sandwiched between the fixed portion 18 of the distal portion 16 of the main body 12 and the proximal portion 14 of the main body 12 for receiving the pneumatically-driven diaphragm 44.

It should be noted that, in operation in the multiport configuration, when internal ports 40, 42 are aligned with external ports 30, 32, external port 28 can be sealed by the tubular body of internal tube 36. Further, when external port 28 is open and uncovered by the tubular body of internal tube 36, internal ports 40, 42 can be out of alignment with external ports 30, 32, thus covering and sealing external ports 30, 32. This alternation of open ports can facilitate aspirating the vitreous through internal tube 36, thus ensuring continuous cutting and flow of tissue.

It is to be understood that the multiport vitrectomy cutter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A multiport vitrectomy cutter adapted to remove vitreous of the eye, comprising:
    a main body having a proximal portion and a distal portion, the proximal portion being adapted for gripping by a user's hand, the distal portion comprising a fixed portion, which is fixed with respect to the proximal portion, and a rotating portion which selectively rotates with respect to the fixed portion;
    an external tube extending from the rotating portion of the distal portion of the main body, the external tube being adapted for penetrating an eye of a patient during an ocular surgical procedure, the external tube having a closed distal end, an open proximal end, and at least three circumferentially separated external ports for receiving vitreous of the eye during an ocular surgical procedure, wherein each of the external ports is located a unique axial distance from the closed distal end and having a portion of the external tube providing a barrier therebetween, each of the external ports is angularly misaligned about a central axis of the external tube by an angle of 120° with respect to one another, thereby providing a 360° cutting ability, further wherein a first external port is located adjacent the closed distal end and has the least axial distance from the closed distal end of the external tube;
    an internal tube having a closed distal end defining a cutting blade, the internal tube being slidably disposed within the external tube, the internal tube having at least a pair of circumferentially separated internal ports defined by a cutting edge adapted to cut vitreous tissue, the external tube being selectively rotatable with respect to the internal tube to selectively align the at least pair of internal ports with second and third external ports thereby selectively exposing either the first external port as a single exposed external port or exposing the second and third external ports as a multiport cutting port configuration, the cutting blade being configured to oscillate across the external ports of the external tube to cut tissue; and
    a pneumatically-driven diaphragm secured to a proximal end of the internal tube for driving the internal tube in a reciprocating motion relative to the external tube.

2. The multiport vitrectomy cutter as recited in claim 1, further comprising a gripping handle secured to the rotating portion of the distal portion of the main body.

3. The multiport vitrectomy cutter as recited in claim 1, further comprising a diaphragm housing sandwiched between the fixed portion of the distal portion of the main body and the proximal portion of the main body for receiving the pneumatically-driven diaphragm.

* * * * *